United States Patent
Xu et al.

(10) Patent No.: US 12,258,351 B2
(45) Date of Patent: Mar. 25, 2025

(54) SESQUITERPENOID DERIVATIVE AND USE THEREOF IN PREPARING BROAD-SPECTRUM ANTIVIRAL DRUG

(71) Applicant: KUNMING UNIVERSITY OF SCIENCE AND TECHNOLOGY, Yunan (CN)

(72) Inventors: Min Xu, Kunming (CN); Shaoxing Dai, Kunming (CN)

(73) Assignee: KUNMING UNIVERSITY OF SCIENCE AND TECHNOLOGY, Kunming (CN)

( * ) Notice: Subject to any disclaimer, the term of this patent is extended or adjusted under 35 U.S.C. 154(b) by 0 days.

(21) Appl. No.: 18/625,188

(22) Filed: Apr. 2, 2024

(65) Prior Publication Data

US 2024/0270754 A1    Aug. 15, 2024

Related U.S. Application Data

(63) Continuation of application No. PCT/CN2022/086210, filed on Apr. 12, 2022.

(30) Foreign Application Priority Data

Mar. 23, 2022   (CN) .......................... 202210291346.6

(51) Int. Cl.
  *C07D 493/10*   (2006.01)
  *A61K 31/35*    (2006.01)
  *A61P 31/14*    (2006.01)

(52) U.S. Cl.
  CPC ............ *C07D 493/10* (2013.01); *A61K 31/35* (2013.01); *A61P 31/14* (2018.01)

(58) Field of Classification Search
  CPC .......... A61P 1/16; A61P 31/20; C07D 493/10; B60K 35/00; B60W 2050/146;
  (Continued)

(56) References Cited

U.S. PATENT DOCUMENTS

2021/0047341 A1* 2/2021 Xu .......................... A61P 31/20

FOREIGN PATENT DOCUMENTS

CN    103880856 A    6/2014
CN    108164545 A    6/2018

OTHER PUBLICATIONS

International Search Report (PCT/CN2022/086210); Date of Mailing: Dec. 15, 2022.

(Continued)

*Primary Examiner* — Savitha M Rao
(74) *Attorney, Agent, or Firm* — W&G Law Group

(57) ABSTRACT

A sesquiterpenoid derivative and use thereof in preparing a broad-spectrum antiviral drug provided. The sesquiterpenoid derivative can stimulate heterogeneous nuclear ribonucleoprotein A2/B1, activate the cell signal pathway of TANK-binding kinase 1-interferon regulatory factor 3, and increase the expression and secretion of endogenous type I interferon. As a result, it can inhibiting various viruses and can be used as a broad-spectrum antiviral drug for preventing or treating various viral infectious diseases and symptoms, including Covid-19, vesicular stomatitis virus VSV-G, AIDS virus, hepatitis C virus, Japanese encephalitis virus, influenza virus, poliovirus, Coxsackie virus, dengue virus, rotavirus, tobacco mosaic virus, measles virus, mumps virus, Ebola virus, Marburg virus, herpes virus and adenovirus. Sesquiterpenoid derivatives can be made as a raw material into oral dosage form such as tablet, capsule and dripping pill, or clinically acceptable pharmaceutical preparation such as inhalant and injection.

5 Claims, 2 Drawing Sheets

(a)

(b)

(58) Field of Classification Search
CPC ........... B60W 30/18; B60W 30/18163; B60W 50/14; B60W 60/001; B62D 15/02; G01C 21/34; G01C 21/3407; G01C 21/3446; G01C 21/3453; G01C 21/3658; G01C 21/3815; G01C 21/387; G05D 1/0088
See application file for complete search history.

(56) References Cited

OTHER PUBLICATIONS

First Office Action(CN202210291346.6); Date of Mailing: Sep. 16, 2023.
A-phytochemical-based-medication-search-for-the-SARS-CoV-2-infection-by-molecular-docking-models-towards-spike-glycoproteins-and-main-proteases.
Research-Progress-on-Chemical-Constituents-and-Pharmacological-Activity-of-Phyllanthus-Acidus.
Anti-Hepatitis-B-Virus-Norbisabolane-Sesquiterpenoids-from-Phyllanthus-acidus-and-the-Establishment-of-Their-Absolute-Configurations-Using-Theoretical-Calculations.
Anti-Coxsackie-Virus-B3-Norsesquiterpenoids-from-the-Roots-of-Phyllanthus-emblica.

\* cited by examiner

SESQUITERPENOID DERIVATIVE AND USE THEREOF IN PREPARING BROAD-SPECTRUM ANTIVIRAL DRUG

CROSS-REFERENCE TO RELATED APPLICATIONS

The present application is a National Stage of International Application No. PCT/CN2022/086210 filed Apr. 12, 2022, which claims priority to Chinese Patent Application No. 2022102913466, filed on Mar. 23, 2022, both of which are hereby incorporated by reference in their entireties.

TECHNICAL FIELD

The present application relates to the technical field of medicine, in particular to a sesquiterpenoid derivative beneficial to treating broad-spectrum viral infectious diseases and symptoms and use thereof.

BACKGROUND

Virus infection has been a constant threat to human life and health. Although specific vaccines and antiviral drugs have showed therapeutic effects, there are still some challenges such as toxicity, drug resistance or the limited ability of vaccines to provide therapeutic benefits. Furthermore, there is a lack of broad-spectrum antiviral drugs to combat the outbreak of certain acute viral infectious diseases, such as the novel coronavirus, which seriously jeopardizes human health and poses a significant threat to public health and safety. Currently, interferon and hormone therapy have achieved certain therapeutic effects during an acute virus outbreaks, but issues like off-target effects and side effects persist. Therefore, the discovery of broad-spectrum antiviral drugs is crucial for addressing the problems of side effects, drug resistance and acute virus outbreak.

Regulating host immunity is a research strategy for developing broad-spectrum antiviral drugs. Dysfunction of immune response is believed to be the primary cause of persistent virus infections. Therefore, enhancing innate immunity and inducing an adaptive immune response against the virus may aid in viral clearance. However, current attempts based on immunization strategy have not been ideal carry risks such as off-target effects and notable side effects. Therefore, a new strategy for broad-spectrum antiviral treatment involves combining effective antiviral drugs with immunotherapy.

SUMMARY

The present application aims to provide a sesquiterpenoid derivative and its use in preparing a broad-spectrum antiviral drug. This derivative has the ability to inhibit RNA and DNA viruses, including Covid-19 (SARS-CoV-2), vesicular stomatitis virus VSV-G, AIDS virus, hepatitis C virus, Japanese encephalitis virus, influenza virus, poliovirus, Coxsackie virus, dengue virus, rotavirus, tobacco mosaic virus, measles virus, mumps virus, Ebola virus, Marburg virus, herpes virus and adenovirus. This dug offers an effective solution as s broad-spectrum antiviral drug with new target spots.

To achieve the above object of the present application, the present application provides the following technical solution: a sesquiterpenoid derivative with a structure represented by the following Structure Formula I, II, III or IV:

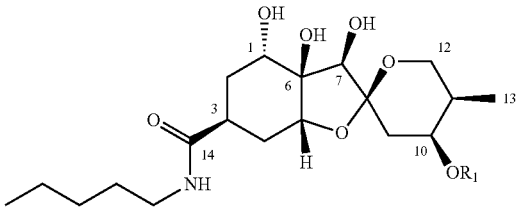

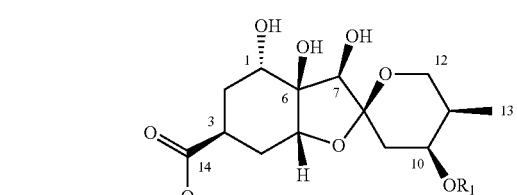

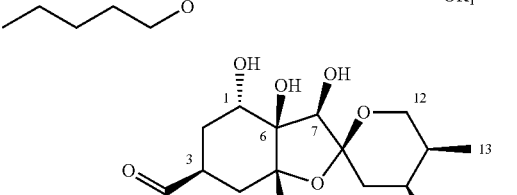

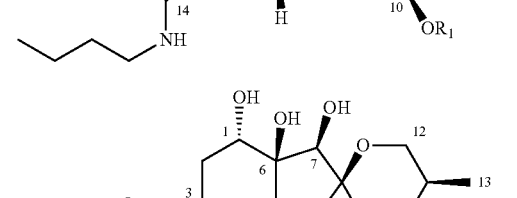

In the Structure Formulas (I) to (IV), $R_1$ is independently selected from a group consisting of a benzoate group, a p-hydroxybenzoate group, a polyhydroxybenzoate group, a p-methoxybenzoate group, a polymethoxybenzoate group, a fluorine-, chlorine- or bromine-substituted benzoate group and hydrogen.

Further, the sesquiterpenoid derivative preferably has a structure represented by Structure Formula I, where $R_1$ is preferably a benzoate group or a p-hydroxybenzoate group.

The present application further provides the use of the above sesquiterpenoid derivative in preparing a drug for treating diseases caused by viral infections.

Further, the viruses include Covid-19, vesicular stomatitis virus VSV-G, AIDS virus, hepatitis C virus, Japanese encephalitis virus, influenza virus, poliovirus, Coxsackie virus, dengue virus, rotavirus, tobacco mosaic virus, measles virus, mumps virus, Ebola virus, Marburg virus, herpes virus and adenovirus.

Further, the sesquiterpenoid derivative is capable of being combined with pharmaceutical carriers and/or edible carriers.

Further, the drug contains the above sesquiterpenoid derivative in a therapeutically effective dosage.

Further, the therapeutically effective dosage is capable of stimulating heterogeneous nuclear ribonucleoprotein A2/B1 (hnRNPA2B1), and activating the TANK-binding kinase 1-interferon regulatory factor 3 (TBK1-IRF3) pathway, which leads to the production of endogenous type I interferon.

Further, the drug includes both oral preparation and non-oral administration preparation. The oral preparation options include tablets, pills, capsules, granules, microcapsule tablets, suspension, dripping pill, and oral liquid. The non-oral administration preparation include injection, aerosol, suppository, and subcutaneous administration dosage forms.

The present application has several beneficial effects that the present application can excite hnRNPA2B1 to form homodimers, and activate a TANK-binding kinase 1-interferon regulatory factor 3 (TBK1-IRF3) pathway, resulting in the generation of endogenous type I interferon, and exhibits remarkable antiviral activity. Compared to current drugs for treating viral infections, the present application has brand-new target spots, which can enhance/improve toxicological safety (i.e., reduce toxicity) and enhance/improve metabolic stability. The present application also has a long half-life and/or less side effects, and at the same time produces a similar or improved biological activity (drug effect). The present application can be used for preventing or treating viral infectious diseases. It can also act as a protective agent for visceral injury, such as liver injury caused by hepatitis B virus. Furthermore, it can be used to study the chemical tools and drugs related to virus infections involving hnRNPA2B1.

The present application can effectively inhibit: Covid-19 (SARS-CoV-2) (with a median effective dose of $IC_{50}$ 485 nM) and vesicular stomatitis virus ($IC_{50}$ 1.72 µM); HIV virus ($IC_{50}$ 1.70 µM), Hepatitis C virus ($IC_{50}$ 551 nM), Japanese encephalitis virus ($IC_{50}$ 1.31 µM), influenza virus ($IC_{50}$ 720 nM), poliovirus ($IC_{50}$ 2.75 µM), Coxsackie virus ($IC_{50}$ 720 nM), dengue virus ($IC_{50}$ 314 nM), rotavirus ($IC_{50}$ 541 nM), tobacco mosaic virus ($IC_{50}$ 1.45 µM), measles virus ($IC_{50}$ 1.62 µM), mumps virus ($IC_{50}$ 1.81 µM) ($IC_{50}$ 1.37 µM), Ebola virus ($IC_{50}$ 1.41 µM), Marburg virus ($IC_{50}$ 1.38 µM), herpes virus ($IC_{50}$ 1.79 µM) and adenovirus ($IC_{50}$ 1.48 µM), which is far better than the positive control, and shows no cytotoxicity at a high concentration of 500 µM; further research showed that the median effective dose in mice was 20 mg/kg, and the maximum single dose of mice per day was 2000 mg/kg, and after 7 days of continuous observation, no toxic reaction occurred. It shows that the drug is effective and low toxic in inhibiting many viruses, and thus can be used as a broad-spectrum antiviral drug.

DESCRIPTION OF EMBODIMENTS

Figure 1:
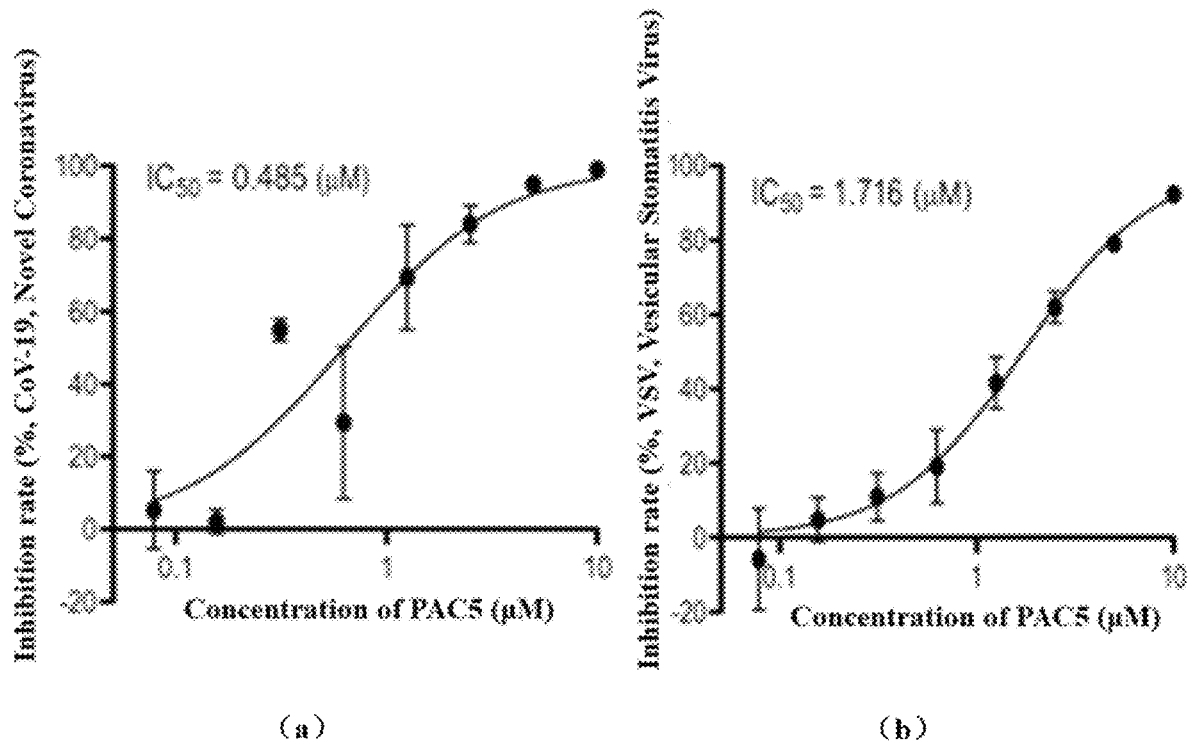
FIG. 1 is a schematic diagram of the virus inhibitory activity of Phyllanthus pentanamide PA-X1 in a cell model, where (a) is a schematic diagram of the inhibitory activity against Covid-19 (SARS-CoV-2) and (b) is a schematic diagram of the inhibitory activity against vesicular stomatitis virus.

It has been found that exciting hnRNPA2B1 and activating the TANK-binding kinase 1-interferon regulatory factor 3 (TBK1-IRF3) pathway leads to the production of endogenous type I interferon, which exhibits significant inhibitory activity against many viruses. Therefore, individuals suffering from this disease can benefit from a composition that contains the pentyl ester or pentanamide of Phyllanthus spp., as described in the present application (or one of analogues and congeners related to the Phyllanthus spp. pentyl ester or pentanamide in structure as one of the main active ingredients).

In addition, the study of hnRNPA2B1 is an important means to explore the development of viral infectious diseases, such as SARS-CoV-2, vesicular stomatitis virus, hepatitis B virus, hepatitis C virus, and visceral damage caused by viruses. The Phyllanthus pentyl ester or pentanamide involved in the present application can significantly increase the expression and secretion of increase endogenous type I interferon IFN-α/β. Therefore, the Phyllanthus pentyl ester or pentanamide involved in this invention (or one of the analogues and congeners related to the Phyllanthus pentyl ester or pentanamide in structure as one of the main active ingredients) can be used to study the pathogenesis of viral infectious diseases.

The Phyllanthus pentyl ester or pentanamide of the present application possesses eight chiral stereocenters, and thus it can be proved to have a better biological activity in racemic (or diastereomer) mixtures, R and S enantiomer (or diastereomer) mixtures or pure enantiomer (R or S) (or diastereomer). When a pure enantiomer shows a better biological activity, it is called a eutomer, while the enantiomer with a lower biological activity is called a distomer.

The Phyllanthus pentyl ester or pentanamide of the present application has three free hydroxyl groups, therefore, the Phyllanthus pentyl ester or pentanamide can be proved to have a better biological activity and/or better metabolic parameters as a salt and/or ester.

The effective pharmaceutical preparation and composition described in this present application can be used for treating various viral infectious diseases and symptoms, such as SARS-CoV-2, vesicular stomatitis virus VSV-G, AIDS virus, hepatitis C virus, Japanese encephalitis virus, influenza virus, poliovirus, Coxsackie virus, dengue virus, rotavirus, tobacco mosaic virus, measles virus, mumps virus, Ebola virus, Marburg virus, herpes virus and adenovirus. Although these drugs are usually used to treat human patients, they can also be used to treat similar or identical diseases of other animals, such as primates, poultry (such as chickens, ducks and geese), farm animals (such as pigs and cows), sports animals (such as racing horse) and pets (such as dogs and cats).

The pharmaceutically acceptable carriers mentioned in this present application include, but are not limited to, calcium carbonate, calcium phosphate, calcium sulfate, sucrose, glucose, lactose, fructose, xylitol, sorbitol, starch, starch paste, cellulose derivatives, gelatin, polyvinylpyrrolidone, sodium chloride, dextrin, stearic acid, magnesium stearate, calcium stearate, vegetable oil, polyethylene glycol, sterile phosphate buffered saline, saline, Ringer's solution and a combination thereof.

The pharmaceutically acceptable salts of the present application include sodium salt, potassium salt, lithium salt, zinc salt, aluminum salt, calcium salt and magnesium salt.

The oral dosage forms of the present application include, but are not limited to, solid oral dosage forms (such as enteric-coated tablets, dropping pills, oral tablets, chewable tablets, granules, powders or capsules) or liquid oral dosage forms (such as syrups or tinctures). In addition, the Phyllanthus pentyl ester or pentanamide and derivatives or compositions thereof can also be added to foods and beverages for oral administration. In addition, the Phyllanthus pentyl ester or pentanamide and derivatives or compositions thereof can also be formulated into chewing gum to promote oral administration and absorption.

The non-oral dosage forms described in the present application include, but are not limited to, administration by injection or other systemic routes, such as transdermal administration or mucosal administration (e.g., nasal, sublingual, buccal, vaginal or rectal administration, via suppository). Other routes of administration (such as those that can be used in veterinary applications) include enteral and parenteral delivery, including intramuscular, subcutaneous and/or intramedullary injection, as well as intrathecal injection, direct intra-cerebroventricular injection, intravenous injection, intraperitoneal injection, intranasal injection or intraocular injection.

The Phyllanthus pentyl ester or pentanamide and derivatives or combinations thereof can also be combined with other pharmaceutical active ingredients to prepare other new pharmaceutical compositions.

The Phyllanthus pentyl ester or pentanamide or any derivative thereof or the combination thereof is used for relieving the above-mentioned symptoms with confirmed curative effect and treatment-related activity.

The therapeutic effect, good drug metabolism parameters and general non-toxicity of the Phyllanthus pentyl ester or pentanamide or any derivative thereof or combination thereof make the compound of the present application an ideal drug for treating the above diseases.

The sesquiterpenoid derivative of the present application has the following Structure Formula:

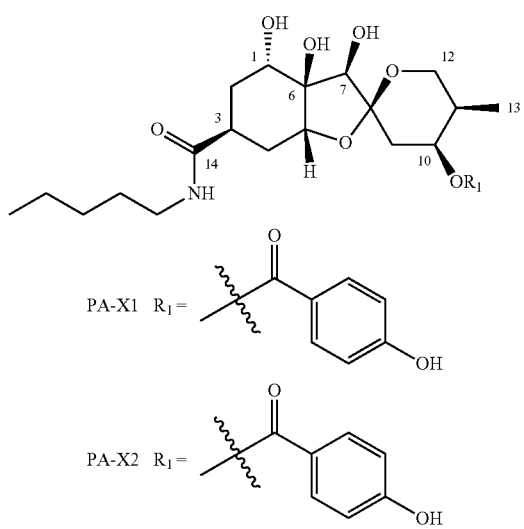

The preparation of the sesquiterpenoid derivative includes the following steps:
1. 10 kg of the rhizome of Phyllanthus spp. was extracted with methanol for three times to obtain 429 g of extractum and the crude extract was dispersed with 5.5 L $H_2O$, and extracted with equal volumes of ethyl acetate and n-butanol for five times, respectively; the n-butanol extraction layer was concentrated to dryness, dissolved in methanol, chromatographed with a macroporous resin column Diaion HP20SS, and eluted with $CH_3OH/H_2O$ (0-100) (V/V %) to obtain five fractions; fractions 2 and 3 were combined, and chromatographed with a Sephadex LH20 ($CH_3OH$ 0-100%) to obtain five fractions; the first two fractions (41.0 g) were combined and then repeatedly chromatographed with a normal phase silica gel column ($CHCl_3$—$CH_3OH$—$H_2O$, 9:1:0-7:3:0.5), a reverse phase RP-8 ($CH_3OH$ 30%-80%) and a gel resin column Toyopearl HW 40C ($CH_3OH$ 0-30%), followed by a preparative high performance liquid chromatography ($CH_3CN$ 15%-30%) to obtain phyllanthacidoid A (10 g) and phyllanthacidoid B (1 g)

2. Phyllanthacidoid A and phyllanthacidoid B ($1.27*10^{-5}$ mol) were dissolved in 1 ml of a 0.72 M potassium carbonate aqueous solution, and hydrolyzed at 60° C. for two hours to produce phyllanthacidoid aglycone A and phyllanthacidoid aglycone B.

3. The phyllanthacidoid aglycone A was dissolved in an organic solvent, and was allowed to react with 20-fold molar equivalents of n-amyl amine for 12 hours at room temperature to generate a compound PA-X1.

4. The phyllanthacidoid aglycone B was dissolved in in an organic solvent, and was allowed to react with 20-fold molar equivalent of n-amyl amine for 12 hours at room temperature to generate a compound PA-X2.

5. The phyllanthacidoid aglycone A was dissolved in an organic solvent, and was allowed to react with 367-fold molar equivalent of n-amyl alcohol for 12 hours at room temperature to generate a compound PA-X3.

6. The phyllanthacidoid aglycone B was dissolved in in an organic solvent, and was allowed to react with 367-fold molar equivalent of n-amyl alcohol at room temperature for 12 hours to generate a compound PA-X4.

7. The phyllanthacidoid aglycone A was dissolved in an organic solvent, and was allowed to react with 20-fold molar equivalent of butylamine for 12 hours at room temperature to generate a compound PA-X5.

8. The phyllanthacidoid aglycone B was dissolved in in an organic solvent, and was allowed to react with 20-fold molar equivalent of n-butylamine for 12 hours at room temperature to generate a compound PA-X6.

9. The phyllanthacidoid aglycone A was dissolved in an organic solvent, and was allowed to react with 367-fold molar equivalent of n-butanol for 12 hours at room temperature to generate a compound PA-X7.

10. The phyllanthacidoid aglycone B was dissolved in in an organic solvent, and was allowed react to with 367-fold molar equivalent of n-butanol at room temperature for 12 hours to generate a compound PA-X8.

In the above steps, the proportions not specified are all molar ratios.

The substantive content of the present application will be further illustrated by the following examples, which however will not limit the present application in any way. Any transformation or substitution based on the present application shall belong to the protection scope of the present application.

Example 1: Synthesis of PA-X1 (PAC5)

Step (1): about 10 mg of phyllanthusol A (PA, phyllanthacidoid A) was placed in a reaction tube. Then 1 ml of a 0.72 M potassium carbonate solution was added. After dissolving, the mixture was placed in an oil bath pot at 60° C. and reacted under magnetic stirring for two hours until the raw materials disappeared; the solution was neutralized to acidity using 1M hydrochloric acid, resulting in a pH value of about 2. A certain amount of saline was added to the solution until the volume reached about 4.5 ml. This was followed by extraction with 4.5×3 ml of ethyl acetate. The organic phases were combined and subjected to reduced pressure distillation to remove the solvent, thereby obtaining a product. Step (2): 10 mg of the product obtained in step (1) was dissolved in 1 ml of DMF dried by a 3A molecular sieve and placed in a reaction tube. Then 20-fold molar equivalent of n-amyl amine was added. Subsequently, 10-fold molar equivalents of HOSU, EDCI and 2-fold molar equivalent of DMAP were added one by one. The mixture was allowed to react overnight at room temperature. The progress of the reaction was monitored by TLC, and it typically took 12 hours to complete. After the reaction was completed, 10% citric acid was added to the reaction solution to 4-5 ml, Then, the extraction with 5×3 ml of ethyl acetate. The organic phases were combined, concentrated and dissolved in approximately 7 ml of dichloromethane. If precipitation occurred, a very small amount of methanol (methanol content was less than 5%) could be added to assist dissolution. The resulting solution was then subjected to separation and purification using amino silica gel to obtain PA-X1 with a yield of about 51%.

Spectral data of PA-X1: ESI-MS: m/z 508 $[M+H]^+$; $^1H$ NMR (600 MHZ, MeOD) δ 7.86 (ddd, J=8.8, 2.7, 2.0 Hz, 2H, H-16, H-20), 6.73 (ddd, J=8.8, 2.7, 2.0 Hz, 2H, H-17, H-19), 5.12 (brd, J=2.6 Hz, 1H, H-10), 4.01 (t, J=3.2 Hz, 1H, H-5), 3.93 (t, J=11.4 Hz, 1H, H-12a), 3.79 (dd, J=10.5, 5.6 Hz, 1H, H-1), 3.65 (s, 1H, H-7), 3.49 (dd, J=11.1, 4.5 Hz, 1H, H-12b), 3.01-2.92 (m, 2H, H-1'), 2.33 (ddd, J=15.1, 11.3, 5.6 Hz, 1H, H-3), 2.10-2.03 (m, 1H, H-9a), 2.02-1.95 (m, 2H, H-11, H-9b), 1.88 (ddd, J=14.6, 11.7, 3.2 Hz, 1H, H-2a), 1.69 (dt, J=14.0, 5.7 Hz, 1H, H-4a), 1.59 (ddd, J=14.4, 5.3, 3.5 Hz, 1H, H-4b), 1.46 (dt, J=13.9, 9.8 Hz, 1H, H-2b), 1.31 (dt, J=14.8, 7.2 Hz, 2H, H-2'), 1.25-1.17 (m, 2H, H-3'), 1.16-1.09 (m, 2H, H-4'), 0.79 (t, J=7.3 Hz, 3H, H-5'), 0.78 (d, J=6.9 Hz, 3H, H-13).

Example 2: Synthesis of PA-X2

Step (1): about 10 mg of phyllanthusol B (PB) was placed in a reaction tube, and 1 ml of a 0.72 M potassium carbonate solution was added. After dissolving, the mixture was heated at 60° C. under stirring for two hours until the raw materials disappeared. The solution was neutralized to acidity with 1M hydrochloric acid, resulting in a pH value of about 2. A certain amount of saline was added into the solution until the volume reached about 4.5 ml, The solution was then extracted with 4.5×3 ml of ethyl acetate, and the organic phases were combined to be subjected to reduced pressure distillation to remove the solvent, thereby obtaining a product. Step (2): 10 mg of the product obtained in step (1) was dissolved in 1 ml of DMF dried by a 3A molecular sieve and placed in a reaction tube, and 20-fold molar equivalent of n-amyl amine was added. Next, 10-fold molar equivalents of HOSU, EDCI and 2-fold molar equivalent of DMAP were added, respectively. The mixture was allowed to react overnight at room temperature. The reaction progress was monitored by TLC, and the reaction was usually completed after 12 hours. After the reaction was completed, 10% citric acid was added to the reaction solution to 4-5 ml, followed by extraction with 5×3 ml of ethyl acetate. The organic phases were combined, concentrated and dissolved with about 7 ml of dichloromethane. If there was precipitation, a very small amount of methanol (methanol content was less than 5%) could be added to assist dissolution, followed by separation and purification with amino silica gel to obtain PA-X2 with a yield of about 44%.

Spectral data of PA-X2: ESI-MS: m/z 514 [M+Na]$^+$; $^1$H NMR (600 MHZ, MeOD) δ 8.00 (brdd, J=8.3, 1.3 Hz, 2H, H-16, H-20), 7.49 (brt, J=7.4 Hz, 1H, H-18), 7.37 (brt, J=7.8 Hz, 2H, H-17, H-19), 5.18 (brd, J=2.6 Hz, 1H, H-10), 4.02 (t, J=3.3 Hz, 1H, H-5), 3.95 (t, J=11.4 Hz, 1H, H-12a), 3.79 (dd, J=10.5, 5.5 Hz, 1H, H-1), 3.65 (s, 1H, H-7), 3.51 (dd, J=11.1, 4.4 Hz, 1H, H-12b), 3.00-2.89 (m, 2H, H-1'), 2.33 (ddd, J=15.1, 11.3, 5.6 Hz, 1H, H-3), 2.09 (dd, J=14.8, 3.2 Hz, 1H, H-9a), 2.05-1.97 (m, 2H, H-11, H-9b), 1.89 (ddd, J=14.7, 11.6, 3.3 Hz, 1H, H-2a), 1.68 (dt, J=14.0, 5.6 Hz, 1H, H-4a), 1.58 (ddd, J=14.4, 5.4, 3.6 Hz, 1H, H-4b), 1.47 (dt, J=14.0, 9.9 Hz, 1H, H-2b), 1.30 (dt, J=14.4, 7.2 Hz, 2H, H-2'), 1.24-1.17 (m, 2H, H-3'), 1.12 (tdd, J=9.6, 7.0, 3.7 Hz, 2H, H-4'), 0.80 (t, J=7.2 Hz, 3H, H-5'), 0.79 (d, J=7.2 Hz, 3H, H-13).

Example 3: Synthesis of PA-X5

Step (1): about 10 mg of phyllanthusol A (PA) was placed in a reaction tube, and 1 ml of a 0.72 M potassium carbonate solution was added; after dissolving, the mixture was put into an oil bath pot at 60° C. and reacted under magnetic stirring for two hours until the raw materials disappeared; the solution was neutralized to acidity with 1M hydrochloric acid, with a PH value of about 2; a certain amount of saline was added into the solution until the volume was about 4.5 ml, followed by extraction with 4.5×3 ml of ethyl acetate, and organic phases were combined to be subjected to reduced pressure distillation to remove the solvent, thereby obtaining a product. Step (2): 10 mg of the product obtained in step (1) was dissolved in 1 ml of DMF dried by a 3A molecular sieve and placed in a reaction tube, and 20-fold molar equivalent of n-butylamine was added; then 10-fold molar equivalents of HOSU, EDCI and 2-fold molar equivalent of DMAP were added respectively, and the mixture was allowed to react overnight at room temperature; the reaction of raw materials was monitored by TLC, and the reaction was usually completed after 12 hours; after the reaction was completed, 10% citric acid was added to the reaction solution to 4-5 ml, followed by extraction with 5×3 ml of ethyl acetate; the organic phases were combined, concentrated and dissolved with about 7 ml of dichloromethane; if there was precipitation, a very small amount of methanol might be added to assist dissolution (methanol content was less than 5%), followed by separation and purification with amino silica gel to obtain PA-X5 with a yield of about 49%.

Spectral data of PA-X5: ESI-MS: m/z 516 [M+Na]$^+$; $^1$H NMR (600 MHZ, MeOD) δ 7.97 (ddd, J=8.82, 2.64, 2.04 Hz, 2H, H-17, H-21), 6.84 (ddd, J=8.82, 2.70, 1.98 Hz, 2H, H-18, H-20), 5.24 (br d, J=2.5 Hz, 1H, H10), 4.12 (t, J=3.2 Hz, 1H, H-5), 4.05 (t, J=11.4 Hz, 1H, H-12), 3.91 (dd, J=10.5, 5.6 Hz, 1H, H-1), 3.76 (s, 1H, H-7), 3.61 (dd, J=11.0, 4.4 Hz, 1H, H-12), 3.09 (br ddd, J=13.3, 7.1, Hz, 2H, H-1'), 2.44 (ddd, J=15.0, 11.3, 5.6 Hz, 1H, H-3), 2.21-2.04 (m, 3H, H-11H-9), 2.00 (ddd, J=14.7, 9.4, 3.2 Hz, 1H, H-2), 1.81 (dt, J=14.0, 5.7 Hz, 1H, H-4), 1.70 (ddd, J=14.4, 5.3, 3.5 Hz, 1H, H-4), 1.58 (dt, J=14.0, 9.8 Hz, 1H, H-2), 1.43-1.36 (m, 2H, H-2'), 1.33-1.25 (m, 2H, H-3'), 0.92 (t, J=7.4 Hz, 3H, H-4'), 0.90 (d, J=6.9 Hz, 3H, H-13).

Example 4: Synthesis of PA-X7

The product obtained in step (1) in Example 1 (the dosage of the raw material PA was about 10 mg) was dissolved in 0.5 ml of DMF dried by a 3A molecular sieve, and then was placed in a reaction tube; 367-fold molar equivalent of n-butanol was added, and the mixture was stirred and mixed, and then 10-fold molar equivalent of EDCI and 2-fold molar equivalent of DMAP were added; the mixture was allowed to react overnight at room temperature, and the reaction of the raw materials was monitored by TLC, and the reaction was usually completed after 12 hours; after the reaction was completed, 10% citric acid was added to the reaction solution to 4-5 ml, followed by extraction with 5×3 ml of ethyl acetate; the organic phases were combined, concentrated and then dissolved with 7 ml of dichloromethane; if there was precipitation, a very small amount of methanol might be added to assist dissolution (methanol content was less than 5%), followed by separation and purification with amino silica gel to obtain a product, with a yield of about 60%; the reaction was monitored by thin layer chromatography, and the reaction was usually completed after 12 h; after the reaction was completed, EtOAc was added to the reaction mixture, followed by purification by amino silica gel to obtain a pure target product with a yield of about 49%.

Spectral data of PA-X7: ESI-MS: m/z 517 [M+Na]$^+$; PA-X7 的波谱数据: : ESI-MS: m/z 517 [M+Na]$^+$; 1H NMR (600 MHZ, MeOD) δ 7.97 (br d, J=8.7 Hz, 2H, H-17, H-21), 6.83 (br d, J=8.7 Hz, 2H, H-18, H-20), 5.22 (br d, J=2.5 Hz, 1H, H-10), 4.11-3.97 (m, 4H, H-5, H-12, H-1'), 3.81 (dd, J=11.0, 4.5 Hz, 1H, H-1), 3.81 (s, 7-H), 3.62 (dd, J=11.1, 4.6 Hz, 1H, H-12), 2.54 (qd, J=11.3, 5.7 Hz, 1H, H-3), 2.17-2.07 (m, 3H, H11, H-9), 2.01-1.91 (m, 2H, H-2, H-4), 1.86 (ddd, J=14.5, 11.5, 3.1 Hz, 1H, H-4), 1.60-1.55 (m, 3H, H-2, H-2'), 1.39-1.32 (m, 2H, H-3'), 0.95 (t, J=7.41 Hz, 3H, H-4'), 0.91 (t, J=6.93 Hz, 3H, H-13).

Example 5: In Vitro Activity Test Against Covid-19 Virus (SARS-CoV-2) and Vesicular Stomatitis Virus (VSV)

293T/ACE2 or Huh-7 cells were inoculated into 24-well plates with a density of 10$^4$ cells per well; after incubation for one night, a proper amount of Covid-19 SARS-CoV-2 or vesicular stomatitis virus VSV-G was added respectively; after 12 hours of infection, the culture solution was replaced by a new culture solution containing different concentrations of test samples; after passage for 3 days, the cells were lysed with 50 μL of a lysing agent (Promega) for 15 minutes; then, synergistic HTX (Bio Tek, USA) was used to measure luminescence when adding luciferase to measure the substrate (Promega, USA), the activity of luciferase was quantified, and the median inhibitory concentrations of the test samples were calculated, which were Covid-19 (SARS-CoV-2) (median effective dose IC$_{50}$ 485 nM, as shown in FIG. 1($a$)) and vesicular stomatitis virus (IC$_{50}$ 1.72 Mm, as shown in FIG. 1($b$)).

Example 6: Study on Antivirus Mechanism of Up-Regulating Endogenous Type I Interferon IFN-α/β

Figure 2:
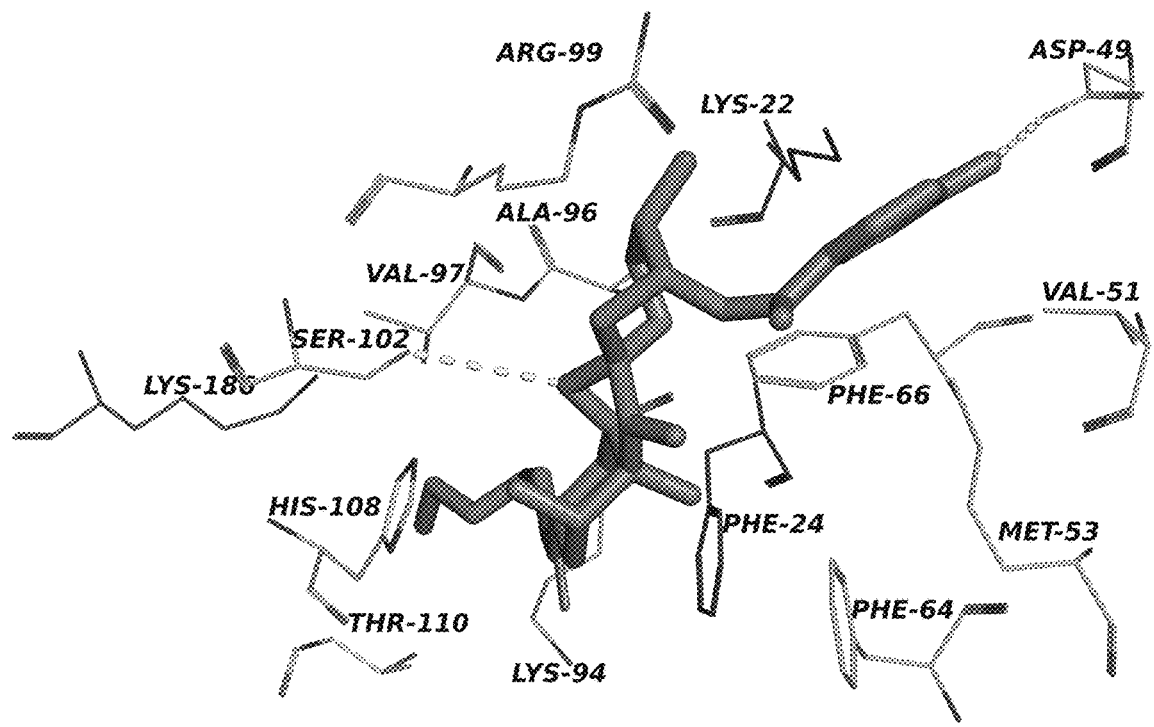
FIG. 2 is a schematic diagram of Phyllanthus pentanamide PA-X1 up-regulating endogenous type I interferon IFN-β.
Figure 3:
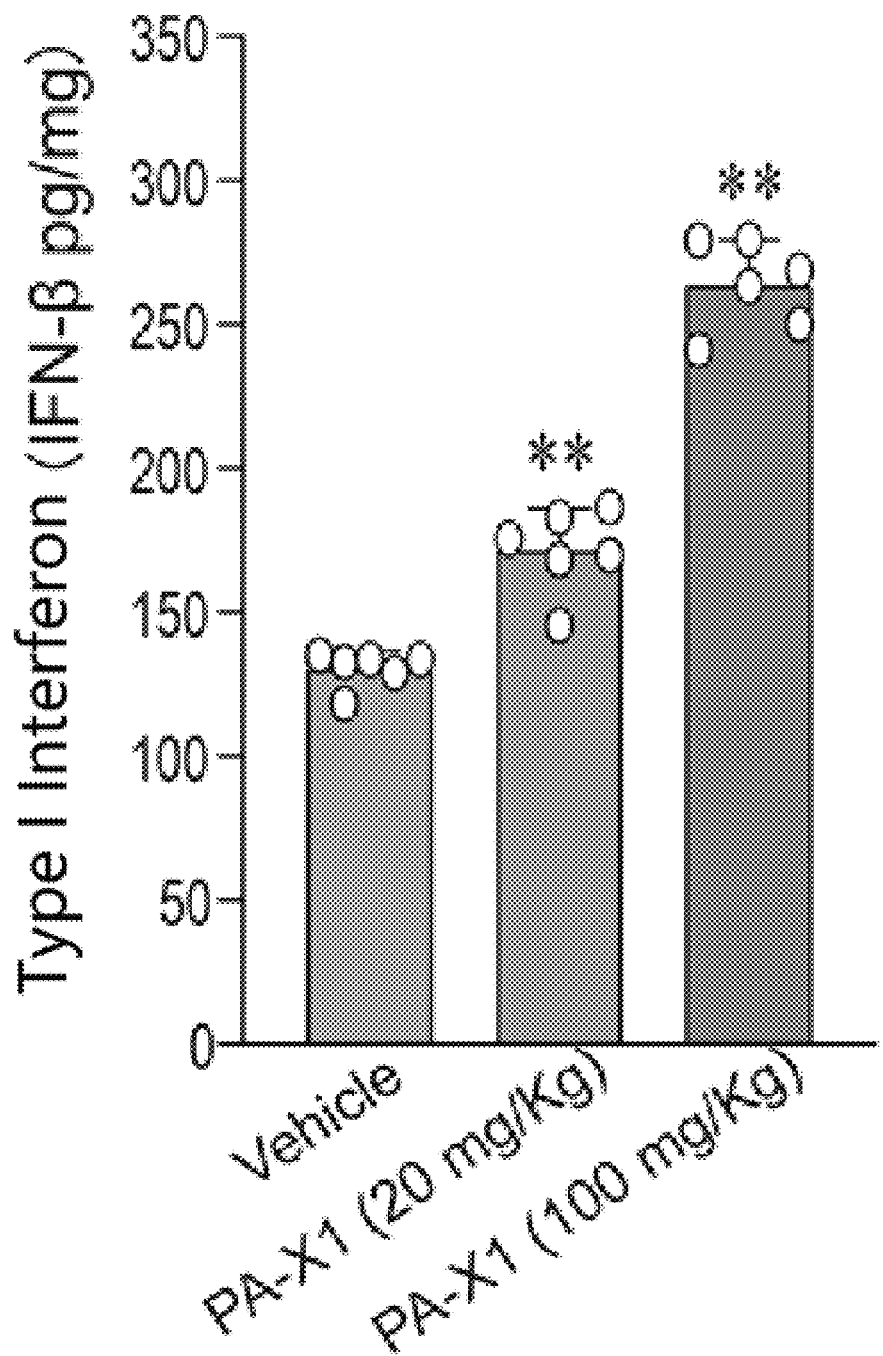
FIG. 3 illustrates the binding pattern of Phyllanthus pentanamide PA-X1 and hnRNPA2B1.

It was found in study that PAC5 bound to the pocket near Asp49 in the RNA recognition motif 1 (RRM1) of hnRNPA2B1 (FIG. 2), which activated hnRNPA2B1 protein, enhanced phosphorylation of TBK1 and IRF3, led to the start of the TBK1-IRF3 pathway, activated the type I IFN signaling pathway, and significantly increased the production of IFN-β in virus-infected mice (FIG. 3).

Example 7: Preparation of PA-X1 Tablets 1000 g of PA-X1 and 1000 g of medicinal starch were mixed evenly and granulated with a proper amount of ethanol as a binder, followed by drying, granulation by a granulator and tableting; 0.30 g per tablet, p.o., 1-2 tablets each time, twice daily.

Example 8: Preparation of PA-X1 Capsules 1000 g of PA-X1 and 1000 g of medicinal starch were mixed evenly and granulated with a proper amount of ethanol as a binder, followed by drying and granulation by a granulator, and then packed into 0 #g capsules; 0.30 g per capsule, p.o., 1-2 capsules each time, twice daily.

Example 9: Preparation of PA-X1 Granules

PA-X1 was granulated by a granulator and then subpackaged; p.o., 5 g each time, twice daily.

Example 10: Preparation of PA-X1 Beverage 100 g of PA-X1, 1000 mL of edible purified water, 500 g of powdered sugar, a proper amount of a stabilizer and a flavoring agent were evenly mixed, and packaged; p.o., 10 mL each time, twice daily.

Example 11: Preparation of PA-X2 Tablets 1000 g of PA-X2 and 100 g of medicinal starch were evenly mixed, and granulated with a proper amount of ethanol as a binder, followed by drying, granulation by a granulator and tableting; 0.30 g per tablet, p.o., 1-2 tablets each time, twice daily.

Example 12: Preparation of PA-X2 Capsules 1000 g of PA-X2 and 100 g of medicinal starch were evenly mixed, and granulated with a proper amount of ethanol as a binder, followed by drying and granulation by a granulator, and then packed into 0 #g capsules; 0.30 g per capsule, p.o., 1-2 capsules each time, twice daily.

Example 13 Preparation of PA-X2 Granules

PA-X2 was granulated by a granulator and then subpackaged; p.o., 5 g each time, twice daily.

Example 14: Preparation of PA-X2 Beverage 100 g of PA-X2, 1000 mL of edible purified water, 500 g of powdered sugar, a proper amount of a stabilizer and a flavoring agent were evenly mixed and packaged; p.o., 10 mL each time, twice daily.

What is claimed is:

1. A method for treating diseases caused by infection of a virus, comprising
administering the compound of Formula I to a subject in need of treatment thereof,
wherein the compound of Formula I has a following structure:

wherein, $R_1$ is p-hydroxybenzoyl group, and
wherein the viruse is selected from a group consisting of Covid-19 and vesicular stomatitis virus.

2. The method according to claim 1, wherein the compound of Formula I is combined with a pharmaceutical carrier and/or an edible carrier for administration.

3. The method according to claim 1, wherein the compound of Formula I is contained in a drug in a therapeutically effective dosage for administration.

4. The method according to claim 3, wherein the therapeutically effective dosage activates heterogeneous nuclear ribonucleoprotein A2/B1 and up-regulates endogenous type I interferon.

5. The method according to claim 3, wherein the drug is selected from a group consisting of tablet, pill, capsules, granules, suspension, dripping pill, oral liquid preparation, injection, aerosol, suppository, and subcutaneous administration dosage form.

* * * * *